(12) United States Patent
Barbera-Guillem

(10) Patent No.: US 6,333,110 B1
(45) Date of Patent: *Dec. 25, 2001

(54) FUNCTIONALIZED NANOCRYSTALS AS VISUAL TISSUE-SPECIFIC IMAGING AGENTS, AND METHODS FOR FLUORESCENCE IMAGING

(75) Inventor: Emilio Barbera-Guillem, Powell, OH (US)

(73) Assignee: Bio-Pixels Ltd., Westerville, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/394,635

(22) Filed: Sep. 13, 1999

Related U.S. Application Data

(63) Continuation-in-part of application No. 09/372,729, filed on Aug. 11, 1999.
(60) Provisional application No. 60/107,829, filed on Nov. 10, 1998.

(51) Int. Cl.$^7$ .............................. A61K 49/00; B05D 7/00; B32B 9/00; B32B 9/04; H01L 29/04
(52) U.S. Cl. .................. 428/402.24; 428/404; 257/65; 257/614; 257/642; 424/9.1; 424/9.32; 424/9.36; 424/9.42; 424/9.6; 427/213.3; 427/214; 427/215; 427/220
(58) Field of Search ................ 428/402.24, 404; 257/65, 614, 642; 424/9.1, 9.32, 9.36, 9.42, 9.6; 427/213.3, 214, 215, 220

(56) References Cited

U.S. PATENT DOCUMENTS

| | | |
|---|---|---|
| 5,990,479 | 11/1999 | Weiss et al. . |
| 6,114,038 * | 9/2000 | Castro et al. .................. 428/402.24 |
| 6,207,392 | 3/2001 | Weiss et al. . |

OTHER PUBLICATIONS

Bruchez et al., Semiconductor Nanocrystals as Fluorescent Biological Labels; Science, Sep. 25, 1998, vol. 281:2013–2015.
Chan and Nie, Quantum Dot Bioconjugates for Ultrasensitive Nonisotopic Detection; Science, Sep. 25, 1998, vol. 281:2016–2018.
Quantum Dots meet Biomolecules; Sep. 28, 1998; C&EN; p. 8.

* cited by examiner

Primary Examiner—Nathan M. Nutter
(74) Attorney, Agent, or Firm—M. Bud Nelson

(57) ABSTRACT

Provided is a method of fluorescence imaging of living tissue using functionalized nanocrystals. The method comprises contacting an effective amount of functionalized nanocrystals with the living tissue; exposing the tissue to a spectrum of light suitable for exciting functionalized nanocrystals, present in fluorescently labeled tissue, to emit a emission spectrum comprising a fluorescence peak; and detecting any fluorescence peak emitted by the tissue exposed to the excitation spectrum of light, and obtaining a fluorescence image of the tissue. Also provided is a composition comprising a functionalized nanocrystal which is bound to a substrate in a living tissue.

10 Claims, 3 Drawing Sheets

US 6,333,110 B1

FUNCTIONALIZED NANOCRYSTALS AS VISUAL TISSUE-SPECIFIC IMAGING AGENTS, AND METHODS FOR FLUORESCENCE IMAGING

This is a continuation-in-part application of copending U.S. Ser. No. 09/372,729 filed Aug. 11, 1999, assigned to the Assignee of the present invention, and the disclosure of which is herein incorporated by reference.

This application claims benefit of Provisional Ser. No. 60/107,829, filed Nov. 10, 1998.

FIELD OF INVENTION

This invention relates a method of using functionalized nanocrystals as imaging agents that enhance imaging of living tissue; and further, to an optic system to provide true color fluorescence images of tissues labeled with the functionalized nanocrystals according to the method of the present invention.

BACKGROUND OF THE INVENTION

Visual imaging of molecules and/or processes ongoing in living tissue is an area of scientific and medical importance which, despite scientific advances, is still underdeveloped. Visualization of soft tissue is of particular value to the medical imaging industry and to the pharmaceutical industry. In medical imaging, there is a constant need for imaging agents (contrast agents or diagnostic agents) that enhance the assessment of one or more of healthy tissue, a disease process affecting tissue, and a disease state of affected tissue. Typically, medical imaging involves delivery of an imaging agent to an organ or tissue to be imaged. Generally, an organ or tissue is imaged is to determine the presence or absence of a suspected abnormality. As to the pharmaceutical industry, in drug development it is particularly important to monitor one or more of: (a) the distribution of the drug in a particular target organ or tissue; (b) the interaction of the drug with living cells of the organ or tissue; (c) internalization of the drug by tissue cells, when the target of action is intracellular; and (d) metabolism or bioclearance of the drug in living tissues.

Typically, conventional fluorescent labels (e.g., fluorescein, rhodamine, phycoerythrin, an the like) are used to study biochemical, pharmacological, or pathological changes that occur in tissue by first fixing the tissue. However, such fluorescent labels are not suitable for all biological applications. For example, conventional fluorescent labels are generally toxic to living cells and tissues comprised of living cells. Additionally, conventional fluorescent labels generally suffer from short-lived fluorescence; e.g., undergo photobleaching after minutes of exposure to an excitation light source. Thus, they would not be suitable for visual imaging requiring any significant length of time needed to ascertain the complexities of a biological process. Further, conventional fluorescent labels are sensitive to changes in environment which can decrease their quantum yield; e.g., brought about by changes in the surrounding pH and dissolved oxygen. Changes in the surrounding pH and dissolved oxygen are conditions that typically may be encountered in living tissues (including organs). Another disadvantage of conventional fluorescent labels is that typically the excitation spectrum of a species of fluorescent label may be quite narrow. However, even when a single light source is used to provide a single excitation wavelength (in view of the spectral line width), often there is insufficient spectral spacing between the emission optima of different species of fluorescent labels to permit individual and quantitative detection without substantial spectral overlap. Thus, when using a combination of different fluorescent labels, multiple filters are typically needed to detect the resultant emission spectra of the combination. Conventional fluorescent labels are limited in sensitivity and resolution of imaging due to the limitations of intensity, photobleaching, and the finite number of molecules which can be used to label a substrate.

Semiconductor nanocrystals ("quantum dots") are known in the art. Generally, quantum dots can be prepared which result in relative monodispersity; e.g., the diameter of the core varying approximately less than 10% between quantum dots in the preparation. Examples of quantum dots are known in the art to have a core selected from the group consisting of CdSe, CdS, and CdTe (collectively referred to as "CdX"). CdX quantum dots have been passivated with an inorganic coating ("shell") uniformly deposited thereon. Passivating the surface of the core quantum dot can result in an increase in the quantum yield of the fluorescence emission, depending on the nature of the inorganic coating. The shell which is used to passivate the quantum dot is preferably comprised of YZ wherein Y is Cd or Zn, and Z is S, or Se. Quantum dots having a CdX core and a YZ shell have only been soluble in organic, non-polar (or weakly polar) solvents. Thus, the instability of these quantum dots in aqueous media has limited their usefulness in biological applications.

To make quantum dots useful in biological applications, it is desirable that the quantum dots are water-soluble. "Water-soluble" is used herein to mean sufficiently soluble or suspendable in a aqueous-based solution, such as in water or water-based solutions or physiological solutions, including those used in biological or molecular detection systems as known by those skilled in the art. Typically, CdX core/YZ shell quantum dots are over-coated with trialkylphosphine oxide, with the alkyl groups most commonly used being butyl and octyl. One method to make the CdX core/YZ shell quantum dots water-soluble is to exchange this overcoating layer with a coating which will make the quantum dots water-soluble. For example, a mercaptocarboxylic acid may be used to exchange with the trialkylphosphine oxide coat. Exchange of the coating group is accomplished by treating the water-insoluble quantum dots with a large excess of neat mercaptocarboxylic acid. Alternatively, exchange of the coating group is accomplished by treating the water-insoluble quantum dots with a large excess of mercaptocarboxylic acid in $CHCl_3$ solution (Chan and Nie, 1998, Science 281:2016–2018). The thiol group of the new coating molecule forms Cd (or Zn)—S bonds, creating a coating which is not easily displaced in solution. Another method to make the CdX core/YZ shell quantum dots water-soluble is by the formation of a coating of silica around the dots (Bruchez, Jr. et al., 1998, Science 281:2013–2015). An extensively polymerized polysilane shell imparts water solubility to nanocrystalline materials, as well as allowing further chemical modifications of the silica surface. However, depending on the nature of the coating group, quantum dots which have been reported as water-soluble may have limited stability in an aqueous solution, particularly when exposed to air (oxygen) and/or light. More particularly, oxygen and light can cause the molecules comprising the coating to become oxidized, thereby forming disulfides which destabilize the attachment of the coating molecules to the shell. Thus, oxidation may cause the coating molecules to migrate away from the surface of the nanocrystals, thereby exposing the surface of the nanocrystals in resulting in "destabilized nanocrystals". Destabilized nanocrystals form aggregates when they interact together, and the formation of such aggregates eventually leads to irreversible flocculation of the nanocrystals.

Thus, current fluorescent molecules (fluorescent labels and quantum dots) are not suitable for labeling of live tissues and visual imaging. In that regard, provided herein are fluorescent labels that are: (a) functionalized to enhance stability under the complex conditions of aqueous environments encountered in living tissues (including organs); (b) stable in the varying conditions encountered in labeling protocols for living tissue; (c) non-toxic to living tissue; (d) extremely sensitive in terms of detection, because of their fluorescent properties (e.g., including, but not limited to, high quantum efficiency, resistance to photobleaching, and stability in complex aqueous environments); (e) a class of semiconductor nanocrystals that may be excited with a single wavelength of light resulting in detectable fluorescence emissions of high quantum yield and with discrete fluorescence peaks; and (f) functionalized so as to be bound to an affinity ligand which is used to target the tissue to be imaged by fluorescence.

SUMMARY OF THE INVENTION

The present invention provides a method for fluorescent imaging of living tissue comprising labeling the live tissue with an effective amount of functionalized nanocrystals, exposing the tissue labeled with functionalized nanocrystals to a excitation wavelength, and then detecting and imaging the fluorescence emitted from the tissue. The functionalized nanocrystals comprise quantum dots capped with a capping compound (multiple molecules of capping compound also referred herein, for ease of reference, as a layer of capping compound), diaminocarboxylic acid molecules which are operatively linked to the layer of capping compound (multiple diaminocarboxylic acid molecules also referred to herein for ease of reference as a layer of diaminocarboxylic acid), and an affinity ligand (one or more molecules) which is operatively linked to the diaminocarboxylic acid layer. The functionalized nanocrystals may further comprise one or more operatively linked successive amino acid layers located between the diaminocarboxylic acid layer and the affinity ligand.

In a method of fluorescence imaging of live tissue using functionalized nanocrystals, an effective amount of functionalized nanocrystals may be mixed with a suitable physiologically acceptable carrier (e.g., an aqueous solution); the resultant mixture is then placed in contact with the live tissue to be labeled; the tissue to be imaged is then exposed to a light source comprising an excitation spectrum in the range of from about 190 nm to about 660 nm (the highest functional wavelength for excitation may depend on the wavelength of the maximum peak of the emission spectrum for the color of the lowest wavelength to be detected; e.g., the highest wavelength of the excitation spectrum should not be greater than the lowest wavelength of the emission spectrum sought to be detected); and detected is any emission peak having a narrow spectral band (e.g. between about 10 nm to about 60 nm), and comprising an emission spectrum in the range of from about 400 nm to about 750 nm, wherein any emission peak detected comprises a detectable signal for imaging (one or more of collection, illumination, processing, quantitation, magnification, digitalization, and visualization) the tissue.

Another object of the present invention is to provide a detection system for imaging tissue labeled with an effective amount of functionalized nanocrystals, wherein the detection system is a reflected illumination system comprising a "fluorescence cube". The fluorescence cube is an assembly comprising a housing, an exciter filter, and a dichroic mirror. The cube may further comprise a barrier filter. However, in the detection system according to the present invention, the cube comprises an exciter filter and dichroic mirror combination selected such that, unlike prior art cubes, multicolor fluorescence images can be acquired using a single cube, as obtained by labeling with different species of the functionalized nanocrystals described herein. The fluorescence cube may be used to detect any water-soluble fluorescent nanocrystals for any application in which fluorescent imaging is desired.

The above and other objects, features, and advantages of the present invention will be apparent in the following Detailed Description of the Invention when read in conjunction with the accompanying drawings.

DETAILED DESCRIPTION OF THE INVENTION

Definitions

Figure 1:
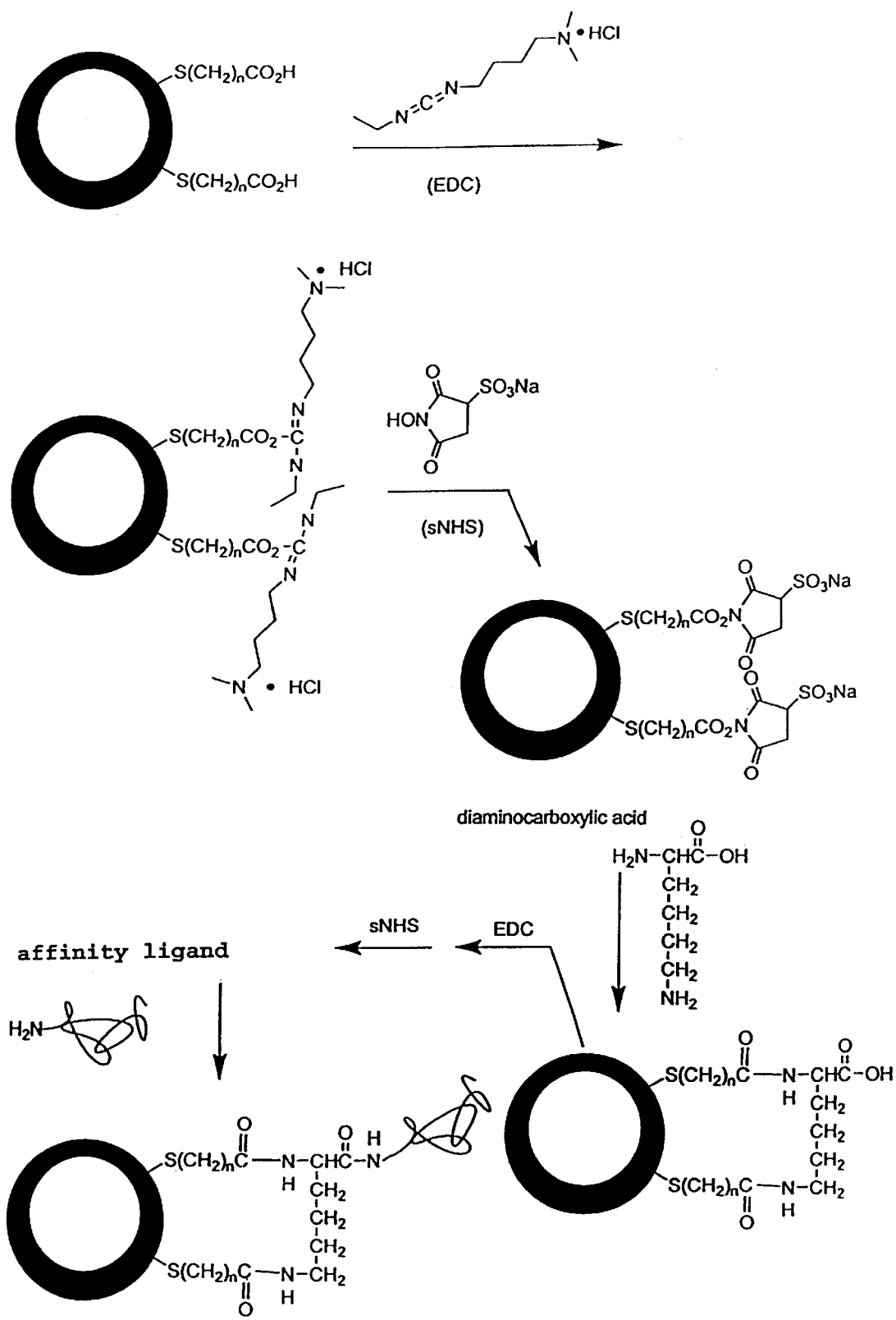
FIG. 1 is a schematic illustrating chemically modifying a water-soluble quantum containing a layer of a capping compound to further comprise a layer of a diaminocarboxylic acid, and a layer of an affinity ligand (e.g., lectin).

By the term "substrate" is meant, for the purposes of the specification and claims to refer to a molecule of an organic nature (e.g., microorganism (bacterial, viral, etc.) or tissue component) or inorganic nature (e.g., chemical that may be present in tissue), the presence and/or quantity of which is being tested for; and which contains a molecular component (domain or sequence or receptor or epitope or portion or chemical group or determinant) for which the affinity ligand has binding specificity. The molecule may include, but is not limited to, a nucleic acid molecule, protein, glycoprotein, eukaryotic or prokaryotic cell, lipoprotein, peptide, carbohydrate, lipid, phospholipid, aminoglycans, chemical messenger, biological receptor, structural component, metabolic product, enzyme, antigen, drug, therapeutic, toxin, inorganic chemical, organic chemical, and the like. The substrate may be extracellular, intracellular, in vivo, in vitro, in situ, or ex vivo.

By the term "affinity ligand" is meant, for purposes of the specification and claims, to mean a molecule which has binding specificity and avidity for a molecular component of, or associated with, a substrate. In general, affinity ligands are known to those skilled in the art to include, but are not limited to, lectins or fragments (or derivatives) thereof which retain binding function; monoclonal antibodies ("mAb", including chimeric or genetically modified monoclonal antibodies (e.g., "humanized")); peptides; aptamers; nucleic acid molecules (including, but not limited to, single stranded RNA or single-stranded DNA, or single-stranded nucleic acid hybrids); avidin, or streptavidin, or avidin derivatives; a drug; and the like. The invention may be practiced using a preferred affinity ligand to the exclusion of affinity ligands other than the preferred affinity ligand. The term "monoclonal antibody" is also used herein, for purposes of the specification and claims, to include immunoreactive fragments or derivatives derived from a mAb molecule, which fragments or derivatives retain all or a portion of the binding function of the whole mAb molecule. Such immunoreactive fragments or derivatives are known to those skilled in the art to include F(ab')$_2$, Fab', Fab, Fv, scFV, Fd' and Fd fragments. Methods for producing the various fragments or derivatives from mAbs are well known in the art (see, e.g., Plückthum, 1992, *Immunol. Rev.* 130:152–188). For example, F(ab')$_2$ can be produced by pepsin digestion of the monoclonal antibody, and Fab' may be produced by reducing the disulfide bridges of F(ab')$_2$ fragments. Fab fragments can be produced by papain digestion of the monoclonal antibody, whereas Fv can be prepared according to methods described in U.S. Pat. No. 4,642,334. Single chain antibodies can be produced as described in U.S. Pat. No. 4,946,778. The construction of chimeric antibodies is now a straightforward procedure (Adair, 1992, *Immunological Reviews* 130: 5–40,) in which the chimeric antibody is made by joining the murine variable region to a human constant region. Additionally, "humanized" antibodies may be made by joining the hypervariable regions of the murine monoclonal antibody to a constant region and portions of variable region (light chain and heavy chain) sequences of human immunoglobulins using one of several techniques known in the art (Adair, 1992, supra; Singer et al., 1993, *J. Immunol.* 150:2844–2857). Methods for making a chimeric non-human/human mAb in general are described in detail in U.S. Pat. No. 5,736,137 (herein incorporated by reference). Aptamers can be made using methods described in U.S. Pat. No. 5,789,157 (herein incorporated by reference). Lectins, and fragments thereof, are commercially available. Lectins are known to those skilled in the art to include, but are not limited to, one or more of *Aleuria aurantia* lectin, *Amaranthus caudatus* lectin, Concanavalin A, *Datura stramonium* lectin, *Dolichos biflorus* agglutinin, soybean agglutinin, *Erythrina cristagalli* lectin, *Galanthus nivalis* lectin, *Griffonia simplicifolia* lectins, Jacalin, *Macckia amurensis* lectins, *Maclura pomifera* agglutinin, *Phaeolepiota aurea* lectins 1 and 2, *Phaseolus vulgaris* lectins, Ricin A, *Moluccella laevis* lectin, peanut agglutinin, *Bauhinia purpurea* agglutinin, *Ricinus communis* agglutinins, *Sambucus nigra* lectin, *Vicia villosa* agglutinin, *Sophora japonica* agglutinin, *Caragana arborescens* agglutinin, *Helix aspersa* agglutinin, *Limax flavus* lectin, limulin, wheat germ agglutinin, and *Ulex europaeus* agglutinin. Nucleic acid molecules may be synthesized using any one of several methods known in the art.

By the term "operably linked" is meant, for purposes of the specification and claims to refer to fusion or bond or an association of sufficient stability to withstand conditions encountered in a method of detection, between a combination of different molecules such as, but not limited to, between the quantum dot and a capping compound, between a capping compound and a diaminocarboxylic acid, between a diaminocarboxylic acid and a diaminocarboxylic acid, between a diaminocarboxylic acid and an affinity ligand, between a diaminocarboxylic acid and an amino acid, and between an amino acid and an affinity ligand, and a combination thereof. As known to those skilled in the art, and as will be more apparent by the following embodiments, there are several methods and compositions in which two or more molecules may be operably linked utilizing reactive functionalities. Reactive functionalities include, but are not limited to, bifunctional reagents/linker molecules, biotin, avidin, free chemical groups (e.g., thiol, or carboxyl, hydroxyl, amino, amine, sulfo, etc.), and reactive chemical groups (reactive with free chemical groups).

By the term "linker" is meant, for purposes of the specification and claims to refer to a compound or moiety that acts as a molecular bridge to operably link two different molecules, wherein one portion of the linker is operably linked to a first molecule, and wherein another portion of the linker is operably linked to a second molecule. The two different molecules may be linked to the linker in a step-wise manner. There is no particular size or content limitations for the linker so long as it can fulfill its purpose as a molecular bridge. Linkers are known to those skilled in the art to include, but are not limited to, chemical chains, chemical compounds, carbohydrate chains, peptides, haptens, and the like. The linkers may include, but are not limited to, homobifunctional linkers and heterobifunctional linkers. Heterobifunctional linkers, well known to those skilled in the art, contain one end having a first reactive functionality to specifically link a first molecule, and an opposite end having a second reactive functionality to specifically link to a second molecule. As illustrative examples, to operably link a hydroxyl group of a polynucleotide strand to an amino group of a diaminocarboxylic acid, the linker may have: a carboxyl group to form a bond with the polynucleotide, and a carboxyl group to form a bond with the diaminocarboxylic acid (see, e.g., U.S. Pat. Nos. 5,792,786, and 5,780,606 for various linkers known in the art). Heterobifunctional photoreactive linkers (e.g., phenylazides containing a cleavable disulfide bond) are known in the art. For example, a sulfosuccinimidyl-2-(p-azido salicylamido) ethyl-1,3'-dithiopropionate contains a N-hydroxy-succinimidyl group reactive with primary amino groups, and the phenylazide (upon photolysis) reacts with any amino acids. The linker may further comprise a protective group which blocks reactivity with a functional group on the linker which is used to react with and bind to a molecule to be linked. A deprotection reaction may involve contacting the linker to one or more conditions and/or reagents which removes the protective group, thereby exposing the functional group to interact with the molecule to be linked. Depending on the nature of the protective group, deprotection can be achieved by various methods known in the art, including, but not limited to photolysis, acidolysis, hydrolysis, and the like. Depending on such factors as the molecules to be linked, and the conditions in which the method of detection is performed, the linker may vary in length and composition for optimizing such properties as flexibility, stability, and resistance to certain chemical and/or temperature parameters. For example, short linkers of sufficient flexibility include, but are not limited to, linkers having from 2 to 10 carbon atoms (see, e.g., U.S. Pat. No. 5,817,795).

By the term "diaminocarboxylic acid" is meant, for purposes of the specification and claims to refer to an amino acid that has two free amine groups. The amino acid may be a naturally occurring amino acid, a synthetic amino acid, a modified amino acid, an amino acid derivative, an amino acid precursor (e.g., citrulline and ornithine are intermediates in the synthesis of arginine), or a combination thereof. In a preferred embodiment, the diaminocarboxylic acid contains neutral (uncharged) polar functional groups which can hydrogen bond with water, thereby making the diaminocarboxylic acid (and the quantum dot to which it is made a part of) relatively more soluble in aqueous solutions containing water than those with nonpolar functional groups. Exemplary diaminocarboxylic acids include, but are not limited to, lysine, asparagine, glutamine, arginine, citrulline, ornithine, 5-hydroxylysine, djenkolic acid, β-cyanoalanine, a synthetic diaminocarboxylic acid (e.g., such as 3,4-diaminobenzoic acid, 2,3-diaminopropionic acid, 2,4-diaminobutyric acid, 2,5-diaminopentanoic acid, 2,6-diaminopimelic acid), and a combination thereof.

By the term "amino acid" is meant, for purposes of the specification and claims to refer to a molecule that has at least one free amine group and at least one free carboxyl group. The amino acid may have more than one free amine group, or more than one free carboxyl group, or may further comprise one or more free chemical reactive groups other than an amine or a carboxyl group (e.g., a hydroxyl, a sulfhydryl, etc.). The amino acid may be a naturally occurring amino acid, a synthetic amino acid, a modified amino acid, an amino acid derivative, and an amino acid precursor. The amino acid may further be selected from the group consisting of a monoaminocarboxylic acid, and a diaminocarboxylic acid. In a preferred embodiment, the monoaminocarboxylic acid contains one or more neutral (uncharged) polar functional groups which can hydrogen bond with water, thereby making the monoaminocarboxylic acid (and the quantum dot to which it is made a part of) relatively more soluble in aqueous solutions containing water than those with non-polar functional groups. Exemplary monoaminocarboxylic acids include, but are not limited to, glycine, serine, threonine, cysteine, β-alanine, homoserine, γ-aminobutyric acid, homocysteine, and a combination thereof.

By the term "capping compound" is meant, for purposes of the specification and claims to refer to a compound having the formula $HS(CH_2)_nX$, wherein X is a carboxylate (carboxylic moiety). "n" is a number in the range of from 1 to about 20, and preferably greater than 4. The thiol group of the capping compound forms Cd (or Zn)—S bonds (depending on whether the shell is Cd or Zn), creating a layer which is not easily displaced in solution. This is an improvement over the use of a capping layer comprised of trialkylphosphine oxide ("TOPO"), in which a dative bond is formed between the oxide and the cadmium (or zinc); and which is readily displaced in the presence of other Lewis bases such as pyridine. Additionally, the carboxylic acid moiety of the capping compound imparts water solubility to the quantum dots. Exemplary capping compounds according to the present invention include, but are not limited to, mercaptocarboxylic acid, or mercaptofunctionalized amines (e.g., aminoethanethiol-HCl, homocysteine, or 1-amino-2-methyl-2-propanethiol-HCl), or a combination thereof.

By the term "living tissue" is meant, for purposes of the specification and claims to refer to a biological tissue (also including an organ) which is not fixed or frozen at the time of contact by, and labeling with, the functionalized nanocrystals in the method according to the present invention (e.g., the tissue has one or more natural physiological functions ongoing, as known to those skilled in the art). Thus, the method of the invention specifically described herein excludes contacting and labeling fixed (e.g., formalin fixed, or alcohol fixed) tissue or single cells with functionalized nanocrystals. However, the term "living tissue" is also meant, for purposes of the specification and claims, to refer to a biological tissue which is living at the time of contact by, and labeling with, functionalized nanocrystals, but is subsequently processed by one or more of freezing, fixing, sectioning, counterstaining, mounting, and the like, prior to exposing the tissue to an excitation wavelength.

By the term "functionalized nanocrystals" is meant, for purposes of the specification and claims to refer to quantum dots comprised of (in order): a core of CdX wherein X is Se or Te or S; passivated with a shell preferably comprised of YZ wherein Y is Cd or Zn, and Z is S, or Se; a capping compound; with at least one additional layer comprising amino acid that functionalizes the nanocrystal, wherein each layer contains neutral (uncharged) polar functional groups which can hydrogen bond with water, and may further comprise one or more free chemical reactive groups; and affinity ligand (one or more molecules thereof). In a preferred embodiment, the at least one additional layer of amino acid that functionalizes the nanocrystal is comprised of diaminocarboxylic acid, and any layers additional thereon may be comprised of amino acid. The term "functionalized nanocrystals" is also used herein to mean, when specifically referring to the method of fluorescence imaging of live tissue and/or to visualization of fluorescence images using a detection system according to the present invention, functionally equivalent quantum dots as will be apparent to those skilled in the art from the descriptions herein. Generally, "functionally equivalent" quantum dots comprise semiconductor nanocrystals that have all of the following properties: are a class of different species of quantum dots that can be excited with a single wavelength of light resulting in detectable fluorescence emissions of high quantum yield, and with discrete fluorescence peaks (e.g. having a narrow spectral band such as between about 10 nm to about 60 nm); are functionalized to be water-soluble and to enhance stability under the complex conditions of aqueous environments encountered in living tissues and in protocols for labeling tissues, hence, are enabled for fluorescently labeling living tissue; are substantially non-toxic to living tissue (e.g., such that they can be used to label living tissue or cell processes active in living tissue); are sensitive in terms of being detected in fluorescence imaging of tissue because of their fluorescent properties (e.g., including, but not limited to, high quantum efficiency, resistance to photo-bleaching, and stability in complex aqueous environments); and are functionalized so as to be bound to affinity ligand which is used to target one or more substrates in tissue to be imaged by fluorescence.

By the term "effective amount" is meant, when used in conjunction with functionalized nanocrystals and for purposes of the specification and claims, to refer to an amount of functionalized nanocrystals sufficient to contact the substrate, if present in the tissue to be fluorescence imaged, and an amount which, when excited with an appropriate excitation wavelength, will emit fluorescence emission wavelength sufficient for detecting and imaging the fluorescently labeled tissue. As apparent to one skilled in the art, such an amount will vary depending on factors which include, but are not limited to, the amount of tissue to be imaged, the amount of substrate that may be present, the rate of contact of the functionalized nanocrystals with the tissue, any abnormalities of the tissue that may affect the efficiency of the functionalized nanocrsytals contacting or binding to substrate in the tissue, and the system used to detect and image fluorescently labeled tissue.

In a preferred embodiment of a method of fluorescence imaging of living tissue according to the present invention, functionalized nanocrystals comprise quantum dots which are functionalized by the addition of a first layer comprising capping compound, a second layer comprising diaminocarboxylic acid, and affinity ligand operably linked to the diaminocarboxylic acid layer. The functionalized nanocrystals are first contacted with a sample under conditions suitable for the nanocrystals to contact and bind, via the affinity ligand portion, the substrate, if present, in the sample being analyzed for the presence or absence of the substrate. Alternatively, the functionalized nanocrystals may comprise quantum dots which are functionalized by the addition of a first layer comprising capping compound, a second layer comprising diaminocarboxylic acid, a third layer comprising amino acid, and operably linked to the amino acid layer is affinity ligand. In another embodiment, one or more additional layers comprising amino acid are added successively before affinity ligand is added and operably linked thereto. In each of the embodiments, the component of each successive addition is operably linked to the component of any contacting layer, as will be more apparent from the figures and following description. These functionalized nanocrystals: may be excited with a single wavelength of light; when excited, result in a detectable light emission (e.g., fluorescence emission) of high quantum yield (e.g., a single quantum dot having at a fluorescence intensity greater than that of at least 10 rhodamine molecules); emit a light emission having a discrete fluorescence peak; and are water-soluble. Also, as related to the method of labeling live tissue according to the present invention, an effective amount of the functionalized nanocrystals is substantially non-toxic. Functionalized nanocrystals typically should have a substantially uniform size of less than 100 Angstroms, and preferably have a substantially uniform size in the range of sizes of from about 2 nm to about 10 nm (diameter). Preferred quantum dots used in the production of functionalized nanocrystals are comprised of a core of CdX wherein X is Se or Te or S. Such CdX quantum dots are passivated with an overlayering ("shell") uniformly deposited thereon, wherein the shell is preferably comprised of YZ wherein Y is Cd or Zn, and Z is S, or Se.

EXAMPLE 1

In this embodiment is illustrated the production of functionalized nanocrystals. Exemplary quantum dots comprise a CdSe core, and a ZnS shell, "(CdSe)ZnS". TOPO capped CdSe were produced by placing TOPO (5 g) in a vessel, and dried at 150° C. for 1 hour under vacuum. The vessel was then backfilled with argon and heated to 300° C. In a controlled environment, $CdMe_2$ (7.2 $\mu l$, 0.1 mmol) and 1 M trioctylphosphine-Se solution (90 $\mu l$, 0.09 mmol) and trioctylphosphine (5 ml) were mixed, and then placed into an injector. This mixture was added to the TOPO in a reaction vessel, previously removed from the heat, in a single continuous injection with vigorous stirring, thereby resulting in the temperature decreasing to about 180° C. The reaction vessel was then subjected to heat to raise the temperature 5° C. every 10 minutes. Aliquots may be removed from the reaction vessel at various time intervals (5 to 10 minutes) to monitor the increase in size of nanocrystals over time, by the observation of the absorption spectra. The temperature may be changed, or the reaction halted, upon reaching nanocrystals of the desired characteristics. For example, the reaction vessel was cooled to about 60° C., 40 ml of methanol was added to cause the nanocrystals to flocculate. After centrifugation, a brightly colored liquid layer of nanocrystals dissolved in trioctylphosphine remained. The methanol/TOPO layer was decanted off, and pyridine (10 ml) was added to the nanocrystal solution and allowed to stand for at least one hour. The nanocrystals were then precipitated as a powder by addition of hexanes, and separated by centrifugation. The powder was washed once more with hexanes, then dissolved in 30 ml pyridine, and centrifuged to remove any reaction byproducts.

To prepare (CdSe)ZnS nanocrystals, the pyridine solution (30 ml) was placed in a reaction vessel, rigorously degassed with an inert gas (e.g., argon), and refluxed for one hour before adjusting the temperature to approximately 100° C. Equimolar amounts of diethyl zinc (zinc source) and hexamethyldisilathiane (sulfide source) were dissolved in trioctylphosphine (2–4 ml) in a controlled environment (glove box) and loaded into an injector. A reaction vessel containing the CdSe dots dispersed in pyridine was heated under an atmosphere of argon, and the Zn and S were added dropwise, via the injector, with vigorous stirring of the mixture for 5–10 minutes. The mixture was left stirring for several hours. After cooling, the pyridine solution was centrifuged to remove any insoluble material. The over-coated nanocrystals were stored in this solution to ensure that the surface of the nanocrystals remained passivated with pyridine.

To prepare nanocrystals which are water soluble, the pyridine overcoating of the (CdX) core/YZ shell nanocrystals were exchanged with a capping compound which contributes to the water-solubility of the resultant nanocrystals. For example, a capping compound comprising mercaptocarboxylic acid may be used to exchange with the pyridine overcoat. Exchange of the coating group is accomplished by treating the water-insoluble, pyridine-capped quantum dots with a large excess of neat mercaptocarboxylic acid. To accomplish this, the pyridine-capped (CdSe)ZnS quantum dots were precipitated with hexanes, and then isolated by centrifugation. The residue was dissolved in neat mercaptoacetic acid, with a few drops of pyridine added, if necessary, to form a transparent solution. The solution is allowed to stand at room temperature for at least six hours. Longer incubation times lead to increased substitution by the thiol. Overnight incubations are ideal. Chloroform is added to precipitate the nanocrystals and wash away excess thiol. The nanocrystals were isolated by centrifugation, washed once more with chloroform, and then washed with hexanes. The residue was briefly dried with a stream of argon. The resultant nanocrystals, coated with the capping compound, were then soluble in water or other aqueous solutions. The nanocrystals, in an aqueous solution, were centrifuged once more, filtered through a 0.2 $\mu$m filter, degassed with argon, and stored in an amber vial. Failure to protect the nanocrystals, in solution, from air and light leads to irreversible flocculation, usually within a week. Although proper storage conditions can extend the shelf life of these water-soluble nanocrystals to several months, there is a drawback because of their sensitivity to oxidation, and a need for repeatedly degassing the vial after each use. As mentioned previously, oxidation may result in the capping compound becoming destabilized (e.g., individual molecules of the capping compound form disulfides, and lose contact with the shell of the nanocrystal); and destabilization can result in irreversible flocculation of the nanocrystals.

Thus, single-site attachment of the capping compound (a mercaptocarboxylic acid; e.g., mercaptoacetic acid, mercaptopropionic acid, mercaptoundecanoic acid, etc.) suffers from limited stability in aqueous solution in the presence of water when exposed to air (oxygen) and light. To improve solubility and stability of the nanocrystals capped with the capping compound, the nanocrystals were overlayered with an organic molecule comprising a diaminocarboxylic acid in forming a functionalized nanocrystal. In a preferred embodiment, the diaminocarboxylic acid (a) contributes to the water-solubility of the functionalized nanocrystal because it has polar functional groups which can hydrogen-bond with water; (b) has at least two free functional groups which are carboxyl-reactive, thereby enabling the diaminocarboxylic acid molecule to operably link to and crosslink carboxyl groups extending from the capping compound on the capped nanocrystals; and (c) once operably linked to the capping compound, has one or more free functional groups which can be used for operably linking an affinity ligand thereto. Regarding stability, crosslinking may hinder the destabilization of single molecules of the capping compound operably linked to the nanocrystals. For example, if two molecules of the capping compound become operably linked to a diaminocarboxylic acid, and if one of the two molecules of the capping compound becomes destabilized, the destabilized molecule may be held into place (close proximity and in association) with respect to the shell of the nanocrystal via the other molecule of the capping compound which is operably linked, and crosslinked, to the diaminocarboxylic acid. Additionally, each successive layer of diaminocarboxylic acid (and/or amino acid, and/or affinity ligand) may further protect the capping compound from oxidation by light and/or air. A single diaminocarboxylic acid molecule has two free amino groups (carboxyl reactive groups) which can operably link to two carboxylic acid groups on the capping compound coating the nanocrystals via the formation of amide bonds. Amide bonds form the backbone of peptide chains, are thermodynamically stable, and may irreversibly cross link the capping compound (e.g., the mercaptoacetic acid coat). Additionally, a free carboxylic acid group on the diaminocarboxylic acid will remain as a site for attachment (operably linking) of other molecules to the diaminocarboxylic acid layer. In a more preferred embodiment, the diaminocarboxylic acid comprises lysine (2,6-diaminohexanoic acid).

For operably linking diaminocarboxylic acid to the capping compound of capped nanocrystals, commercially available crosslinking agents and methods known to those skilled in the art may be used. For example, and as illustrated in FIG. 1, mercaptoacetic acid-capped nanocrystals were dissolved in an aqueous buffer system (pH of about 7). The buffer may comprise such buffers as PBS or HEPES. It is noted that the presence of phosphate has been shown to dramatically decrease the lifetime of the crosslinking agent from hours to minutes. To the capped nanocrystals was added EDC (1-ethyl-3-[3-dimethylaminopropyl] carbdiimide) and sulfoNHS (sulfo-N-hydroxysuccinimide) in 500–1000 times excess. The resulting solution was stirred at room temperature for 30 minutes. Mercaptoethanol was added to neutralize unreacted EDC at 20 mM concentration and stirred for 15 minutes. The entire solution was then added dropwise, with stirring, to a solution of lysine (large excess) in the same buffer; and the mixture was stirred for 2 hours at room temperature. Ethanolamine (30 mM) was added to quench the reaction; and the mixture was stirred for 30 minutes at room temperature or left overnight at 4° C. The solution was centrifuged to remove any precipitated solids, and then ultrafiltered through a 30 kD MW centrifugal filter. The resultant concentrated, functionalized nanocrystals can be solubilized in an aqueous solution of choice. Once solubilized, the resulting solution can be stored in an amber vial under an inert gas to prevent flocculation.

In another embodiment, as also illustrated in FIG. 1, the functionalized nanocrystals comprised of a first layer comprising the capping compound and a second layer comprising a diaminocarboxylic acid, is further functionalized by the addition of affinity ligand. As an illustrative example, a protein (glycoprotein, peptide, lipoprotein, etc.) having a free carboxyl-reactive group (e.g., an amine group) can be operably linked to the free carboxyl group of the diaminocarboxylic acid of the functionalized nanocrystals using methods known in the art. For example, an affinity ligand selected from the group consisting of avidin, a monoclonal antibody, an F' ab fragment, or a lectin, may be operably linked using EDC and sulfo-NHS using the general methods as previously described herein. More particularly, EDC functions to activate at least one reactive functionality (e.g., a carboxylate) to catalyze its reaction with another reactive functionality such as the amine group of a protein. The functionalized nanocrystals (1 ml, $8.1 \times 10^{-9}$ mol) were esterified by treatment with EDC ($8.1 \times 10^{-6}$ mol), followed by treatment with sulfo-NHS ($8.9 \times 10^{-6}$ mol) at ambient temperature in buffered aqueous solution (at about pH 7.4) for 30 minutes. 2-mercaptoethanol was added to the solution at a concentration of 20 mM, and the mixture was stirred for 15 minutes to quench any unreacted EDC. Using lectin wheat germ agglutinin (WGA) as an exemplary affinity ligand, the nanocrystals were then contacted with WGA ($8.1 \times 10^{-9}$ mol in PBS, 1 mg/ml) with vigorous stirring, and the reaction mixture was stirred for 2 hours (e.g., conditions sufficient to form an amide bond between the EDC-activated carboxylates of the diaminocarboxylate layer and the amine groups on WGA in forming functionalized nanocrystals which are water-soluble and have lectin operably linked thereto). Ethanolamine was added at a concentration of 30 mM to quench the coupling reaction, and the reaction mixture was stirred for 30 minutes. The resulting solution was then filtered through a 30 kD molecular weight cutoff centrifugal filter to remove excess reagents. The concentrated material was then diluted to 1 ml in buffer (e.g., PBS) or other suitable aqueous solution. Essentially, the same procedure can be used to operably link avidin, an antibody, or other affinity ligand having at least one free carboxyl-reactive group.

In one embodiment of a method according to the present invention, it may be desirable to attach a plurality of oligonucleotides to the functionalized nanocrystals as affinity ligands for subsequent use in fluorescent imaging of living tissue. In one illustration of this embodiment, the functionalized nanocrystals comprise avidinylated, functionalized nanocrystals (e.g., (CdX) core/YZ shell, capped with the capping compound, layered with a diaminocarboxylic acid with operably linking to the cappping compound, layered with avidin with operably linking to the diaminocarboxylic acid) which are then contacted with, and operably linked to, a plurality of molecules of the desired oligonucleotide, each of which contains one or more biotin molecules (including native biotin or a biotin derivative having avidin-binding activity; e.g., biotin dimers, biotin multimers, carbo-biotin, and the like). Preferably, the oligonucleotides are biotinylated at a single terminus of the strand. Using methods known to those skilled in the art, biotin molecules can be added to or incorporated in a nucleotide strand, and even localized to one terminus, such as by directing synthesis of the nucleotide strands with nucleotides and biotin-nucleotides, or by biotinylating the 5' aminogroup of the nucleotide with sulfo-NHS-biotin. Thus, by contacting avidinylated, functionalized nanocrystals with biotinylated oligonucleotides, formed is a functionalized nanocrystal having a plurality of oligonucleotides extending therefrom (e.g., through the biotinavidin binding, the plurality of oligonucleotides become operably linked to the functionalized nanocrystals). These functionalized nanocrystals may then be used as probes in detecting components of living tissue such as nucleic acid molecules or sequences, or nucleic acid binding proteins, using standard methods known to those skilled in the art.

EXAMPLE 2

Figure 2:
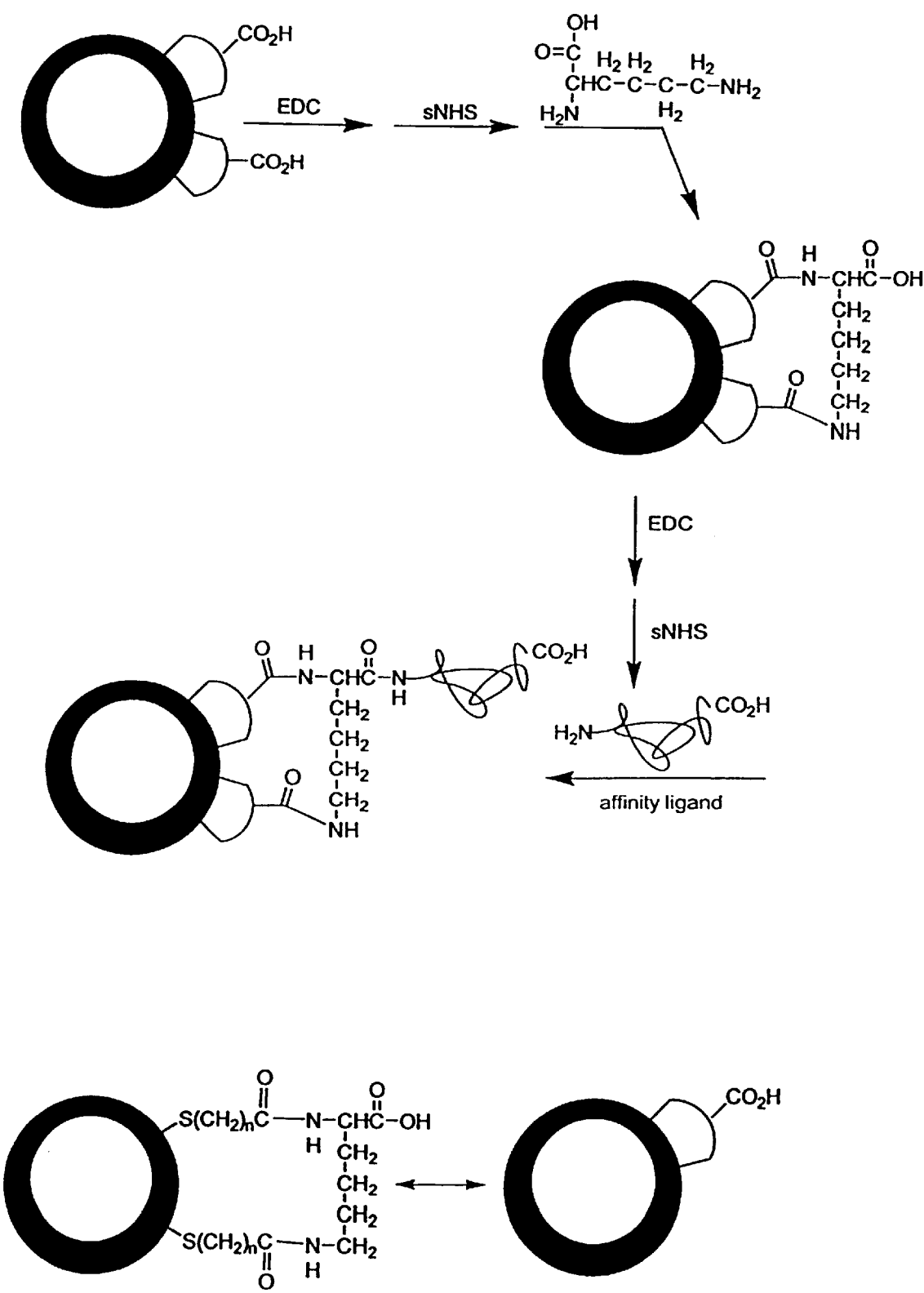
FIG. 2 is a schematic illustrating chemically modifying a water soluble quantum dot containing a layer of a capping compound to further comprise a layer of a diaminocarboxylic acid, an additional layer of a diaminocarboxylic acid, and a layer of an affinity ligand.

In another embodiment, the functionalized nanocrystals comprise quantum dots functionalized by the addition of a first layer comprising capping compound, a second layer comprising diaminocarboxylic acid, and a third layer comprising an amino acid. Functionalized nanocrystals comprising the addition of a first layer comprising capping compound, a second layer comprising diaminocarboxylic acid may be produced using the methods outlined in Example 1. These functionalized nanocrystals are further functionalized by the addition of another layer comprising amino acid, such as illustrated in FIG. 2. FIG. 2 illustrates the addition of an additional layer of amino acid wherein the amino acid comprises a diaminocarboxylic acid. In this illustration, the diaminocarboxylic acid molecules of the third layer can operably link, and crosslink, the free carboxyl groups of the diaminocarboxylic acid molecules of the second layer. Thus, not only does the diaminocarboxylic acid molecules of the third layer contribute to solubility, but may also contribute to further stability to the functionalized nanocrystal (e.g., by adding some protection against oxidation). However, it is also noted that with each diaminocarboxylic acid layer added, the number of free functional groups for reaction to operably link with a subsequent carboxylic acid layer or affinity ligand is reduced. If, for example, an affinity ligand is to be operably coupled to the diaminocarboxylic acid molecules of the third layer, a reduction in the number of free functional groups for reaction with the affinity ligand may be desirable, particularly if it is desired to operably link relatively fewer molecules of the affinity ligand to the functionalized nanocrystals (e.g., because of one or more of the size, chemical characteristics, and specificity of the affinity ligand, or substrate to which the affinity lignd binds). However, if a maximum number of affinity ligands is desired to be operably linked to the functionalized nanocrystals, it may be disadvantageous to use a third layer comprising an amino acid comprising a diaminocarboxylic acid. If a maximum number of affinity ligands is desirable, alternative embodiments include: (a) operably linking the affinity ligand to functionalized nanocrystals comprising a first layer comprising capping compound, and a second layer comprising diaminocarboxylic acid; or (b) operably linking a third layer (comprising an amino acid comprising a monoaminocarboxylic acid) to the second layer comprising the diaminocarboxylic acid, and then operably link affinity ligand to the functionalized nanocrystals via the free carboxyl group of the monoaminocarboxylic acid. Thus, various factors, such as the nature of the affinity ligand to be operably linked, may guide the choice of a carboxylic acid for a third layer in further functionalizing the nanocrystals according to the present invention.

As illustrated in FIG. 2, functionalized nanocrystals comprising the addition of a first layer comprising capping compound, and a second layer comprising diaminocarboxylic acid, are mixed with EDC and sulfo-NHS in 500–1000 times excess. The resulting solution is stirred at room temperature for 30 minutes. Mercaptoethanol is added to neutralize unreacted EDC at 20 mM concentration and stirred for 15 minutes. The entire solution is then added dropwise, with stirring, to a solution of an amino acid comprising a diaminocarboxylic acid (e.g., lysine in large excess) in the same buffer; and the mixture is stirred for 2 hours at room temperature. Ethanolamine (30 mM) is added to quench the reaction; and the mixture is stirred for 30 minutes at room temperature or left overnight at 4° C. The solution is centrifuged to remove and precipitate solids, and then ultrafiltered through a 30 kD MW centrifugal filter. The resultant concentrated, functionalized nanocrystals can be solubilized in an aqueous solution of choice. Once solubilized, the resulting solution can be stored in an amber vial under an inert gas to prevent flocculation. This process can also be used to add a third layer comprising an amino acid comprising a monoaminocarboxylic acid rather than a diaminocarboxylic acid. In either case, functionalized nanocrystals comprising a third layer comprising an amino acid may be further functionalized by operably linking affinity ligand to the free amine reactive group(s) (or other free reactive groups) of the amino acid comprising the third layer using methods previously described herein.

EXAMPLE 3

In a method for fluorescence imaging of living tissue using functionalized nanocrystals, the living tissue is contacted with an effective amount of functionalized nanocrystals in fluorescent labeling the tissue (via the affinity ligand's binding specificity for the substrate, if present, in the living tissue), the tissue is exposed to an excitation spectrum, and then detected and imaged is fluorescence emitted from any of the tissue which is fluorescently labeled. In one illustrative embodiment of the method of fluorescence imaging of live tissue, an effective amount of functionalized nanocrystals may first be mixed with a suitable physiologically acceptable carrier. Physiologically acceptable carriers are known to those skilled in the art to include, but are not limited to, an aqueous solution, buffered solution, water, saline, phosphate buffered saline (PBS), Ringer's injection solution, intravenous bag solutions (e.g., dextrose solution), tissue culture medium, inert oils, and the like. The mixture comprising the functionalized nanocrystals and the suitable physiologically acceptable carrier may comprise a form such as a suspension or a solution or other suitable formulation for the intended purpose. The resultant mixture is then placed in contact with the live tissue to be imaged; the tissue to be imaged is then exposed to a light source comprising an excitation spectrum in the range of from about 190 nm to about 660 nm (the highest functional wavelength for excitation depends on the wavelength of the maximum peak of the emission spectrum for the color of the lowest wavelength to be detected; e.g., the highest excitation wavelength should not exceed the lowest emission wavelength sought to be detected); and detected is any emission peak having a narrow spectral band (e.g. between about 10 nm to about 60 nm), and comprising an emission spectrum in the range of from about 400 nm to about 750 nm (the lowest emission wavelength detectable may depend on the excitation spectrum; e.g., the highest excitation wavelength should not exceed the lowest emission wavelength sought to be detected), wherein any emission peak detected comprises a detectable signal for imaging (one or more of collection, illumination, processing, transmitting, quantitation, magnification, digitalization, and visualization) the tissue.

The imaging of the tissue is dependent upon the presence of the one or more target substrates, in the tissue, for which the affinity ligand of the functionalized nanocrystals has binding specificity. Contact, and subsequent binding, between the affinity ligand of the functionalized nanocrystal and the substrate, if present in the living tissue, results in complexes comprising the functionalized nanocrystal-substrate which can be excited to emit a detectable signal for detection and imaging. It will be apparent to one skilled in the art that multiple species of functionalized nanocrystals may be used in imaging a tissue. Each of the species of functionalized nanocrystals may vary in color (e.g., because of core size or doping agent) and/or in the affinity ligand operatively linked thereto as compared to other species of functionalized nanocrystals used in combination for multicolor imaging. For example, it will be apparent to those skilled in the art that more than one target substrate may be detected, if present in the living tissue, simultaneously by using more than one uniform size of functionalized nanocrystals; with each uniform size having an affinity ligand operably linked thereto which has a different binding specificity (hence can detect a different target substrate) than the affinity ligand operably linked to functionalized nanocrystals of a different uniform size. Thus, in one embodiment, multicolor imaging of one or more substrates in living tissue may be performed simultaneously. In a preferred embodiment wherein multicolor imaging is to be performed, the light source suitable for exciting the multiple species of functionalized nanocrystals may comprise a spectrum (visible, or UV, or a combination thereof) that is suitable for exciting all of the species of functionalized nanocrystals used in the labeling step to emit a respective fluorescence peak. A preferred excitation spectrum for this purpose and for the method according to the present invention, and when the colors are a plurality of colors selected in the spectral range from yellow to violet, is in the range of about 300 nm to about 400 nm; and in a more preferred embodiment, from about 360 nm to about 365 nm.

Any fluorescence peak emitted is then detected and imaged by appropriate detection means or system (e.g., one or more of: photodetector, filter, charge couple device camera (CCD camera) fluorescence microscope, endoscopic imaging system, endoscopic fluorescence imaging microscope, a fiber optic fluorescence imaging microscope, a fluorescence cube, a computer for digitalizing a fluorescence image, and the like). In a preferred embodiment, the appropriate detection means can detect fluorescence peaks in the spectral range of about 400 nm to about 750 nm; and, when more than one color is used to label the tissue, distinguish between discrete fluorescence peaks within that range. Quantitation of the amount of substrate present is directly related to the intensity of an emitted fluorescence peak. As known to those skilled in the art of nanocrystals, the absorbance peak and fluorescence peak emissions depend on properties of the nanocrystals which may include, but are not limited to, the chemical nature, doping agent (if any), and core size. The following are illustrative examples of altering the size of the nanocrystal to achieve a various colors. Functionalized CdSe/ZnS nanocrystals having a substantially uniform size comprising a diameter of about 68.4 angstroms (A) may be excited with light of a spectrum ranging from about 300 nm to about 400 nm, and emit a fluorescence peak (orange) at 609 nm which may be detected using appropriate detection means. Functionalized CdSe/ZnS nanocrystals having a substantially uniform size comprising a diameter of about 53.2 A may be excited with light of a spectrum ranging from about 300 nm to about 400 nm, and emit a fluorescence peak (yellow) at 545 nm which may be detected using appropriate detection means. Functionalized CdSe/ZnS nanocrystals having a substantially uniform size comprising a diameter of about 46.6 A may be excited with light of a spectrum ranging from about 300 nm to about 400 nm, and emit a fluorescence peak (green) at 522 nm which may be detected using appropriate detection means. Functionalized CdSe/ZnS nanocrystals having a substantially uniform size comprising a diameter of about 23 A may be excited with light of a spectrum ranging from about 300 nm to about 400 nm, and emit a fluorescence peak (blue) at 480 nm which may be detected using appropriate detection means.

EXAMPLE 4

In one illustration of a method of fluorescence imaging of living tissue, an effective amount of functionalized nanocrystals are administered in vivo. In vivo imaging of living tissue may allow for imaging of gross tissue morphology, imaging for gross tissue abnormalities, for assisting in surgical removal of imaged tissue, imaging of metabolic processes, imaging for tissue biodistribution studies, or imaging for diagnostic purposes. For example, an effective amount of functionalized nanocrystals are mixed with a physiologically acceptable carrier to result in an injectable composition. In this illustrative embodiment, the injectable composition is administered in vivo to an individual by introducing the injectable composition into a vascular access which is selected because it feeds or drains the living tissue desired to be imaged. After a sufficient time for the fluorescent nanocrystals to reach the tissue to be imaged, and to bind the substrate if present, the tissue to be imaged is then illuminated with an excitation wavelength light source. Such time period may depend on various factors including, but not limited to, the size and weight of the individual, the health of the individual, the metabolic rate of the individual, the vascular access used for administration, the location of the tissue desired to be imaged. An appropriate detection means is placed in proximity of the tissue desired to be imaged, and any fluorescence peak is detected and then used to image the tissue. As apparent to one skilled in the art, the excitation wavelength light source may be coupled with the appropriate detector means. An illustrative example is an apparatus comprising an optic fiber which serves as the excitation wavelength light source; and an endoscope which is suitable for fluorescence imaging (see, e.g., U.S. Pat. No. 5,891,016, the disclosure of which is herein incorporated by reference). An image transmitted from the endoscope may be collected by a fluorescence imaging microscope (e.g., a fiber optic fluorescence imaging microscope), magnified using a microscope objective, collected by a CCD camera, and processed and visualized on a computer monitor.

EXAMPLE 5

In a method for fluorescent imaging of living tissue using functionalized nanocrystals, the living tissue is contacted with an effective amount of the functionalized nanocrystals in fluorescent labeling the tissue, if present in the tissue is the substrate for which the affinity ligand has binding specificity; the tissue is processed; the processed tissue is exposed to a excitation spectrum; and then detected and imaged is fluorescence emitted from any of the tissue which is fluorescently labeled. To illustrate this embodiment, functionalized nanocrystals were produced using methods outlined herein in Example 1 and comprised a core, a shell, a capping compound comprising the formula $HS(CH_2)_nX$ wherein X is a carboxylate, a diaminocarboxylic acid which is operably linked to the capping compound, and WGA which is operably linked to the diaminocarboxylic acid (WGA at a concentration approximated to be about one nanocrystal per lectin molecule). The functionalized nanocrystals were of a monodisperse size for emitting a yellow fluorescence in imaging living tissue comprising liver. The functionalized nanocrystals were used to image liver tissue morphology; and in particular, sinusoidal liver endothelium and its distribution in the liver. The target substrates in the sinusoidal liver endothelium are sinusoidal liver endothelial cells, termed LEC-1 cells, which preferentially express N-acetyl glucosamine in higher concentrations than most other liver endothelial cell populations, and which are adjacent to portal veins ("periportal"). WGA, having binding specificity for N-acetyl glucosamine, was used as the affinity ligand of the functionalized nanocrystals to target the substrate, LEC-1 expressing N-acetyl glucosamine, in the living tissue to be imaged.

In continuing with this illustration, a BALB/c mouse was anesthetized and then placed in a supine position. Heparin (0.1 ml) was administered, and after a ten minute delay, the abdomen was surgically opened. The portal vein was exposed by upward traction on the underside of the liver and downward counter action on the duodenum, and inserted therein was a plastic tube connected to a syringe. Via the syringe, phosphate buffered saline (PBS) was perfused through the liver at a rate of about 0.1 ml per second, for a total of 5–10 ml of perfusion. The PBS and displaced blood was allowed to exit through a severed vein. An effective amount of the functionalized nanocrystals was diluted in 1 ml of PBS, in a final concentration of $8.1 \times 10^{-7}$ M (WGA concentration approximated to be about 29 µg/ml) and the mixture was then perfused at 0.1 ml/second. The mixture was allowed to remain in the liver for about 5 to 10 minutes, and then the liver was perfused again with between 5 to 10 ml of PBS. This perfusion was intended to remove any unbound or non-specifically functionalized nanocrystals from the liver. The liver was removed, and then processed. In this illustration, processing of the tissue comprised freezing the liver in a cryostat ($-20°$ C.), and cutting of frozen sections (5–10µ). Frozen sections were placed on slides within the cryostat, and air-dried at room temperature; some slides were fixed with alcohol; and all slides were treated with mounting fluid and cover-slipped. Various mounting fluids were used; e.g., gel mount, crystal mount, or cytoseal, for microscopy. A few of the sections, before cover-slipping, were also processed by counter-staining with DAPPI for visualization of the nuclei of hepatocytes and endothelial cells (e.g., to give a background which enhanced the contrast and details, such as positioning, of the fluorescing cells of the tissue relative to other cells in the liver).

Figure 3:
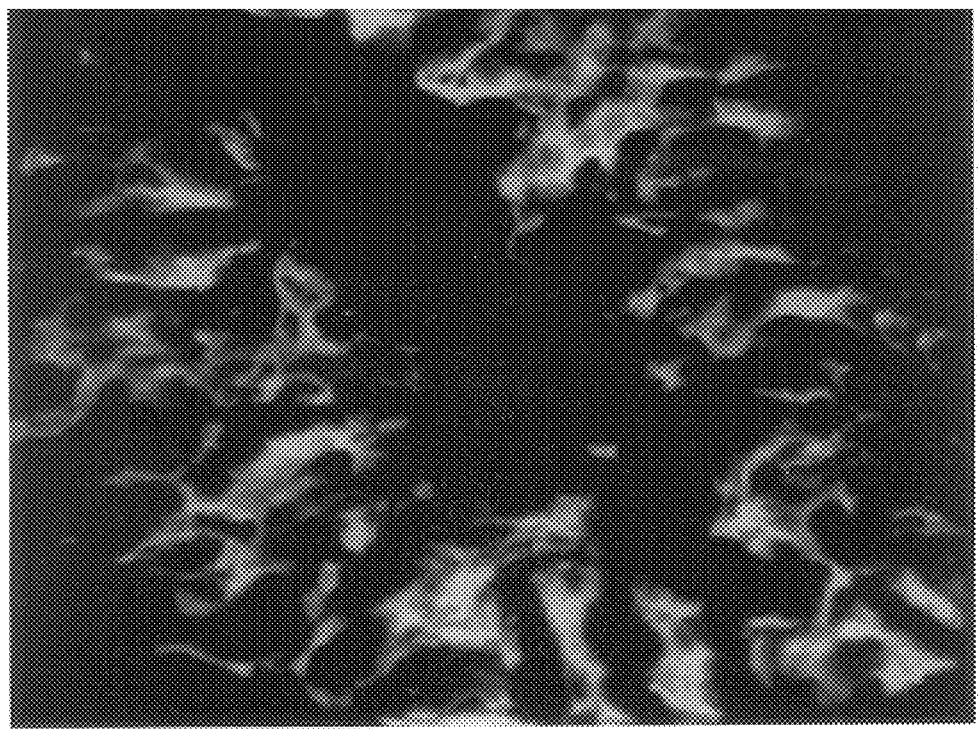
FIG. 3 is a black and white representation of a photographic image showing liver endothelium labeled with an effective amount of functionalized nanocrystals having wheat germ agglutinin as the affinity ligand.

The sections were imaged by a detection system. In a first detection system, a false color image (FIG. 3, shown in black and white) was obtained with a reflected light fluorescence microscope (Olympus BX60 with a reflected light fluorescence attachment, BX-FLA) with an attachment comprising an exciter filter allowing passage of light in the spectral range of from about 300 nm to about 400 nm, a dichroic mirror, and a FITC filter for allowing passage of emitted light of a spectrum ranging from about 450 nm to about 550 nm (to allow detection of the peak emission wavelength of 557 nm) to an attached CCD camera for detection, and then to a computer for processing and imaging the false color image.

Figure 4:
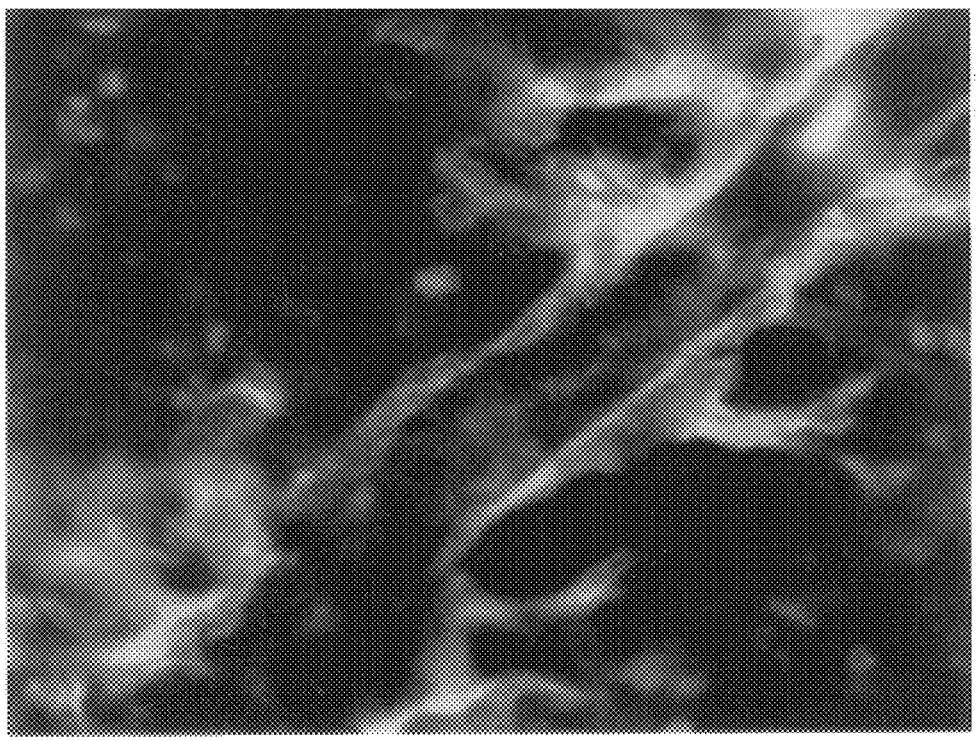
FIG. 4 is a black and white representation of a photographic image showing liver endothelium labeled with an effective amount of functionalized nanocrystals having wheat germ agglutinin as the affinity ligand.

In a second and more preferred detection system, the detection system comprised a fluorescence microscope operatively coupled to a fluorescence cube. The fluorescence cube was designed for use with functionalized nanocrystals to ensure that the sample (e.g., tissue section) is excited by the desired excitation spectrum, and that a fluorescence emission spectra comprising narrow spectral wavelength bands reach the detector (e.g., eye, CCD camera, etc.). In one embodiment, the fluorescence cube comprises a housing, an exciter filter and a dichroic mirror. The light source used with, or part of, the fluorescence microscope is illuminated through an opening in the housing to the excitor filter, wherein the exciter filter allows only light of certain wavelengths to pass through ("incident light"). In a preferred embodiment, the incident light passing through the exciter filter comprises a wavelength ranging from about 200 nm to about 400 nm; and in a more preferred embodiment, the incident light passing through the exciter filter comprises a wavelength band ranging from about 310 nm to about 400 nm with a maximum transmission peak at about 360 nm to about 365 nm; and in another preferred embodiment, the incident light passing through the exciter filter comprises a wavelength band ranging from about 355 nm to about 375 nm with a maximum transmission peak at about 365 nm. In continuing with this illustrative example, the incident light passing through the exciter filter reaches the dichroic mirror. In a preferred arrangement, the dichroic mirror is positioned at an angle of 45° with respect to the optical axis of the incident light, thereby reflecting the light comprising the excitation spectrum through an opening in the housing, towards the objective and through to the sample (e.g., tissue section). If the tissue section is labeled with the functionalized nanocrystals, the functionalized nanocrystals will become excited by the excitation spectrum, and emit an emission spectrum that is dependent on the species of functionalized nanocrystals used to label the tissue. For example, the functionalized nanocrystals comprising WGA as the affinity ligand were of a size to have a peak emission wavelength of about 557 nm. Where a plurality of species of functionalized nanocrystals is used to perform multicolor imaging, the emitted light will comprise a plurality of discrete fluorescence peaks in a spectral range of about 420 nm to about 750 nm, dependent upon the species of functionalized nanocrystals used. Thus, emitted light is passed back up through the objective to the dichroic mirror. The dichroic mirror may be chosen to reflect away unwanted wavelengths of light (e.g., light of a wavelength of less than 400 nm), and allow passage through an opening in the housing to the detector of emitted light comprising the emission spectrum. In a preferred embodiment, the dichroic mirror allows passage to the detector of emitted light of a spectrum ranging from about 415 nm to about 900 nm. The fluorescence cube may further comprise a barrier filter to ensure that blocked out from reaching the detector is any wavelength of light that may be undesirable or harmful (e.g., wavelengths of light less than 400). Using this detection system comprising the fluorescence cube and the fluorescence microscope, a true color image of liver endothelium, and particularly of the distribution of LEC-1 cells labeled with the functionalized nanocrystals, was obtained (FIG.4, black and white image shown). As can be seen in FIG. 3, and more clearly seen in FIG. 4, the functionalized nanocrystals exclusively label the LEC-1 cells that surround the portal domain sinusoids of the imaged liver. No staining occurs outside of this region. This result is consistent with the known lectin-binding patterns of the liver sinusoids. The detection system may further comprise a CCD camera and computer for processing and printing a true color image of the tissue.

EXAMPLE 6

In another illustration of a method for fluorescent imaging of living tissue using functionalized nanocrystals, the living tissue is contacted with effective amounts of different species of functionalized nanocrystals in multicolor fluorescent labeling the tissue (if present in the tissue is the one or more substrates targeted by the functionalized nanocrsytals, the tissue is processed, the processed tissue is exposed to an excitation spectrum, and then detected and imaged is fluorescence emitted from any of the tissue which is fluorescently labeled. To illustrate this embodiment, functionalized nanocrystals were produced using methods outlined herein in Example 1. One species of functionalized nanocrystals was of a monodisperse size for emitting a yellow fluorescence, and contained WGA as affinity ligand which is operably linked to diaminocarboxylic acid (WGA at a concentration approximated to be about one nanocrystal per lectin molecule). Another species of the functionalized nanocrystals was of a monodisperse size for emitting a red fluorescence, and contained Peanut agglutinin (PNA) as the affinity ligand which is operably linked to the diaminocarboxylic acid (PNA at a concentration approximated to be about one nanocrystal per lectin molecule). The two species of functionalized nanocrystals are used to image liver tissue morphology; and in particular, sinusoidal liver endothelium and its distribution in the liver. The target substrate in the sinusoidal liver endothelium for the functionalized nanocrystals having WGA as the affinity ligand are LEC-1 cells, primarily periportal as previously described herein. The target substrates in the sinusoidal liver endothelium for the functionalized nanocrystals having PNA as the affinity ligand are sinusoidal liver endothelial cells, primarily those termed LEC-2 cells and LEC-3 cells, which preferentially express galactosyl (β1,3) N-acetyl galactosamine in higher concentrations than most other liver sinusoidal endothelial cell populations. LEC-2 cells are typically found in the perivenous sinusoidal segments, whereas LEC-3 cells are typically found in the pericentral sinusoidal segments, of liver endothelium. Using the procedures outlined in Example 6 herein, a mouse liver may be perfused with a mixture comprising effective amounts of the two species of functionalized nanocrystals diluted in 1 ml of a physiologically acceptable carrier (e.g., PBS), the mixture is allowed to remain in the liver for about 5 to 10 minutes, the liver is perfused again with between 5 to 10 ml of PBS, and then the liver is removed, and processed. In an alternative and preferred embodiment, and because PNA can, to some degree, bind to a substrate on LEC-1 cells, a mixture comprising functionalized nanocrystals having WGA as affinity ligand is first perfused into the liver, and a sufficient time is allowed for these functionalized nanocrystals crystals to bind LEC-1 cells (and hence assist in minimizing binding of LEC-1 by PNA due to a blocking effect), and then the mixture comprising functionalized nanocrystals having PNA as the affinity ligand is perfused into the liver. In either embodiment, frozen sections may be prepared, and mounted onto slides. The sections may then be imaged by a detection system using a fluorescence microscope and fluorescence cube for detecting functionalized nanocrystals having WGA as the affinity ligand at a peak emission wavelength of about 557 nm, and functionalized nanocrystals having PNA as the affinity ligand at a peak emission wavelength of about 662 nm. The resultant imaging of the tissue may show red fluorescence in a pattern consistent with binding primarily to LEC-2 and LEC-3 cells in the respective perivenous and pericentral sinusoidal segments of the imaged liver section; and yellow fluorescence exclusively in the LEC-1 containing periportal sinusoidal segments of the imaged liver section.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept, and therefore such modifications and/or adaptations are intended to be within the meaning and scope of the appended claims.

What is claimed:

1. A functionalized nanocrystal bound to a substrate in a living tissue, wherein the functionalized nanocrystal comprises: a quantum dot having a core and a shell; a layer comprising capping compound operably linked to the quantum dot, wherein capping compound comprises a compound having the formula $HS(CH_2)_nX$, wherein X is a carboxylate; a layer comprising a diaminocarboxylic acid which is operably linked to capping compound; and affinity ligand which is operably linked to diaminocarboxylic acid.

2. The functionalized nanocrystal bound to a substrate according to claim 1, wherein the core comprises CdX, and wherein X is Se, Te or S.

3. The functionalized nanocrystal bound to a substrate according to claim 1, wherein the shell comprises YZ, and wherein Y is Cd or Zn, and Z is S, or Se.

4. The functionalized nanocrystal bound to a substrate according to claim 1, wherein the capping compound is selected from the group consisting of a mercaptocarboxylic acid, a mercaptofunctionalized amine, aminoethanethiol-HCl, homocysteine, 1-amino-2-methyl-2-propanethiol-HCl, and a combination thereof.

5. The functionalized nanocrystal bound to a substrate according to claim 1, wherein diaminocarboxylic acid is selected from the group consisting of lysine, asparagine, glutamine, arginine, citrulline, ornithine, 5-hydroxylysine, djenkolic acid, β-cyanoalanine, 3,4-diaminobenzoic acid, 2,3-diaminopropionic acid, 2,4-diaminobutyric acid, 2,5-diaminopentanoic acid, 2,6-diaminopimelic acid, and a combination thereof.

6. The functionalized nanocrystal bound to a substrate according to claim 1, wherein the affinity ligand is selected from the group consisting of a lectin, a monoclonal antibody, a peptide, an aptamer, a nucleic acid molecule, avidin, streptavidin, and an avidin derivative.

7. The functionalized nanocrystal bound to a substrate according to claim 1, wherein the functionalized nanocrystal further comprises an amino acid located between the diaminocarboxylic acid and the affinity ligand.

8. The functionalized nanocrystal bound to a substrate according to claim 1, wherein the amino acid is selected from the group consisting of a monocarboxylic acid, and a diaminocarboxylic acid.

9. The functionalized nanocrystal bound to a substrate according to claim 1, wherein the amino acid comprises a diaminocarboxylic acid, and the diaminocarboxylic acid is selected from the group consisting of lysine, asparagine, glutamine, arginine, citrulline, ornithine, 5-hydroxylysine, djenkolic acid, β-cyanoalanine, 3,4-diaminobenzoic acid, 2,3-diaminopropionic acid, 2,4-diaminobutyric acid, 2,5-diaminopentanoic acid, 2,6-diaminopimelic acid, and a combination thereof.

10. The functionalized nanocrystal bound to a substrate according to claim 1, wherein the amino acid comprises a monoaminocarboxylic acid, and the monoaminocarboxylic acid is selected from the group consisting of glycine, serine, threonine, cysteine, β-alanine, homoserine, γ-aminobutyric acid, homocysteine, and a combination thereof.

* * * * *